(12) United States Patent
Corbin et al.

(10) Patent No.: US 6,603,048 B1
(45) Date of Patent: Aug. 5, 2003

(54) PROCESS TO SEPARATE 1,3-PROPANEDIOL OR GLYCEROL, OR A MIXTURE THEREOF FROM A BIOLOGICAL MIXTURE

(75) Inventors: David Richard Corbin, West Chester, PA (US); Tucker Norton, Avondale, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 20 days.

(21) Appl. No.: 09/677,121

(22) Filed: Sep. 29, 2000

Related U.S. Application Data

(60) Provisional application No. 60/157,773, filed on Oct. 5, 1999, and provisional application No. 60/158,204, filed on Oct. 7, 1999.

(51) Int. Cl.[7] .................. C07C 27/26; C07C 29/74; C07C 31/18; C07C 31/22
(52) U.S. Cl. .................. 568/868; 568/869; 568/870
(58) Field of Search .................. 435/250, 247, 435/249, 158, 159, 157; 568/868, 869, 870

(56) References Cited

U.S. PATENT DOCUMENTS

| 4,420,561 A | 12/1983 | Chen et al. |
| 5,008,473 A | 4/1991 | Breitkopf et al. |

FOREIGN PATENT DOCUMENTS

| DE | 86-3632397 | 9/1986 |
| DE | 3632397 | 3/1988 |
| EP | 0101254 | 2/1984 |
| EP | 645371 | 3/1995 |
| JP | 01153058 | * 6/1989 |

OTHER PUBLICATIONS

Malinowski, Janusz.; Evaluation of liquid extraction potentials for downstream separation of 1,3–propanediol; Biotechnology Techniques; 1999; 127–130; 13; Kluwer Academic Publishers.
Günzel, Bernd et al.; Adsorption von Diolen aus Fermantationsmedien an hydrophobe Zeolithe; Chem.–Ing.– Tech.; 1990; 748–750; 62; VCH Verlagsgesellschaft mbH, Weinheim.
Schöllner, R. et al.; Untersuchungen zur adsorptiven Trennung von Glycerol/Propan–1,3–diol in wäaBriger Lösung durch Flüssigphasen–Adsorption an Zeolithen; Journal für praktische Chemie Chemiker–Zeitung; 1994; 404–407; Johann Ambrosius Barth.
Malinowski, Biotech. Prog. 13(2), 127–30 (1999).
Mao et al., J. Liq. Chromatogr. 17(8), 1811–9(1994).
Cameron et al., Biotech. Prog. 14, 116–25(1998).
Guenzel et al., (Chem.–Ing.–Tech.62(9), 748–50(1990).
Schlieker et al., (Chem.–Ing.–Tech. 64(8), 727–8(1992), German Text/Abstract only.
Schoellner et al. (J. Prakt. Chem. 336(5), 404–7 (1994), German Text/Abstract only.
Sano et al., J. Membr. Sci. 95(3), 221–8 (1994).
Guenzel et al., Chem.–Ing.–Tech., 62(9), pp. 748–750, 1999.*
Guenzel et al., DECHEMA Biotechnol. Conf. vol. 4, pp. 713–716, 1990. abstract only.*

* cited by examiner

*Primary Examiner*—Johann Richter
*Assistant Examiner*—Elvis O. Price

(57) ABSTRACT

A process is provided to separate 1,3-propanediol, glycerol, or a mixture of 1,3-propanediol and glycerol from a biological mixture using a molecular sieve.

4 Claims, 6 Drawing Sheets

PROCESS TO SEPARATE 1,3-PROPANEDIOL OR GLYCEROL, OR A MIXTURE THEREOF FROM A BIOLOGICAL MIXTURE

This application claims benefit of Provisional Application No. 60/157,773 filed Oct. 5, 1999 and Provisional Application No. 60/158,204 filed Oct. 7, 1999.

FIELD OF THE INVENTION

This invention relates to processes separating 1,3-propanediol, glycerol, or a mixture of 1,3-propanediol and glycerol from biological mixtures using a molecular sieve.

BACKGROUND OF THE INVENTION 1,3-Propanediol is a key monomer ingredient for polytrimethylene terephthalate (3GT), a high-performance polyester with a variety of applications in apparel, carpet, etc. The cost of 1,3-propanediol synthesis and separation plays a critical role in the total cost of the 3GT polyester.

Various routes to produce 1,3-propanediol are found in the literature. These routes include commercially practiced chemical synthesis routes (e.g., acrolein hydration and subsequent hydrogenation), and an uncommercialized biological route (e.g., from glucose through glycerol to 1,3-propanediol). In either case, the synthesis of 1,3-propanediol results in impurities which must be removed before polymerization. For the acrolein route, these impurities include water, acrolein, and other organic compounds. Similarly, the biological route from glucose can have impurities such as water, glucose, organic acids, salts, glycerol, and other compounds. Given the high boiling point and hydrophilicity of 1,3-propanediol, economic separation of 1,3-propanediol from these contaminants and from reaction by-products and/or reaction co-products by standard means is difficult.

Known processes to purify 1,3-propanediol have serious limitations. Liquid-liquid extraction of aqueous 1,3-propanediol (Malinowski, *Biotech. Prog.* 13(2), 127–30 (1999)) was disclosed as "not good enough to make simple extraction efficient". Another liquid—liquid extraction (DE 86-3632397) uses cyclohexane to extract dimeric acrolein from 1,3-propanediol; however, the process takes longer than 1 hour and is of little use for removing impurities other than acrolein. HPLC separations of 1,3-propanediol (Mao et al. *J Liq. Chromatogr.* 17(8), 1811–9 (1994)) with ion-exclusion or reverse phase methods are well known but can be used only at small scale because of the cost of chromatographic media and high pressure operation. One standard technique to purify the 1,3-propanediol includes evaporation of the process stream followed by distillation, both of which require extensive quantities of heat input and can be costly.

In addition, it is well known that processes to produce 1,3-propanediol can suffer feedback inhibition; that is, particularly for the biological route, the production of high concentrations of 1,3-propanediol can decrease the rate of additional 1,3-propanediol production or cell growth (Cameron et al. *Biotech. Prog.* 14, 116–25 (1998)). Thus, there would be additional value for a separation method capable of use in situ during 1,3-propanediol production.

Selective sorbents such as carbons and zeolites have been proposed for 1,3-propanediol separation. The effectiveness of separation using such sorbents varies with the components of the biological mixture and the sorbents involved. The successful design of sorbent-based systems is considered an important factor in the separation process.

Zeolites can be generically described as complex aluminosilicates characterized by a three-dimensional framework structure enclosing cavities occupied by ions and water molecules, all of which can move with significant freedom within the zeolite matrix. In commercially useful zeolites, the water molecules can be removed from or replaced within the framework without destroying its structure. Zeolites can be represented by the following formula: $M_{2/n}O\cdot Al_2O_3\cdot xSiO_2\cdot yH_2$, wherein M is a cation of valence n, x>2, and y is a number determined by the porosity and the hydration state of the zeolite, generally from 0 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite structure consists of corner-linked tetrahedra with Al or Si atoms at centers of tetrahedra and oxygen atoms at corners. Such tetrahedra are combined in a well-defined repeating structure comprising various combinations of 4-, 6-, 8-, 10-, and 12-membered rings. The resulting framework consists of regular channels and cages, which impart a useful pore structure for separation. Pore dimensions are determined by the geometry of the aluminosilicate tetrahedra forming the zeolite channels or cages, with nominal openings of 0.26 nm for 6-rings, 0.40 nm for 8-rings, and 0.55 nm for 10-rings and 0.74 nm for 12-rings (these numbers assume ionic radii for oxygen). Those skilled in the art will recognize that zeolite with the largest pores being 8-rings, 10-rings, and 12-rings are considered small, medium, and large pore zeolites, respectively. Pore dimensions are critical to the performance of these materials in catalytic and separation applications, since this characteristic determines whether reactant/adsorbent molecules can enter and product molecules (in the catalytic application case) can exit the zeolite framework. In practice, it has been observed that very slight decreases in ring dimensions can effectively hinder or block movement of particular reactants/adsorbent or catalysis products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as $Na^+$ or $K^+$, which are situated in or near 8-ring openings as well as 6-ring openings. Access is enhanced by divalent ions, such as $Ca^{2+}$, which are situated only in or near 6-rings. Thus, KA and NaA exhibit effective pore openings of about 0.3 nm and 0.4 nm respectively, whereas CaA has an effective pore opening of 0.5 nm.

Molecular sieves, of which zeolites are a sub-class, have recently been considered for 1,3-propanediol purification. The zeolites used for 1,3-propanediol purification were not of the proton form and therefore were susceptible to contamination of the mixture or adsorbate through leaching of the cation. Guenzel et al. (*Chem.-Ing.-Tech.* 62(9), 748–50 (1990)) examined de-aluminized NaY and silicalite for separation of 1,3-propanediol/water solutions; they obtained a maximum loading of 0.12 g 1,3-propanediol/g zeolite. However, they did not investigate glycerol selectivity. Schlieker et al. (*Chem. -Ing. -Tech.* 64(8), 727–8 (1992)) used activated carbon, but experienced significant non-specific adsorption of the costly intermediate glycerol and achieved 1,3-propanediol fermentation productivities of only 2.5 g/L hr. Schoellner et al. (*J. Prakt. Chem.* 336(5), 404–7 (1994)) examined two X, two Y, and a Na-ZSM-5 zeolite. The Na-ZSM-5 was found superior to the X and Y zeolites, but again can leach a salt into the mixture or adsorbate stream. The recovery of 1,3-propanediol from the zeolite was not discussed.

Silicalite has been used for ethanol recovery from dilute aqueous solutions. In one implementation (Sano et al. *J Membr. Sci.* 95(3), 221–8 (1994)), silicalite membranes on a stainless steel or alumina support were used as in a pervaporation method to obtain selectivity of greater than 60 for ethanol to water.

Additionally, H-ZSM-5 zeolites have been used as a separation tool of leucine and isoleucine from aqueous solutions (EP 645371). H-ZSM-5 (Si/Al=14) was used to separate isoleucine from leucine in an aqueous mixture, and then the zeolite was regenerated by contact with base, a process which generates waste salts which must be disposed or treated with expensive electrodialysis. Leucine and isoleucine, both six carbon moieties with bulky amine and acid groups, have much greater molecular size than 1,3-propanediol, which has only three carbons. Yonsel, S. et al. reported very low loading of the desired adsorbate, leucine, amounting to less than 0.04 g leucine/g zeolite. Adsorption and desorption of ethanol from zeolites by temperature variation is known in the art, but the case of desorbing a zeolite-adsorbed product with ethanol was not well known. In JP 01153058, separation of flavors from fermentation products is performed by adsorption with zeolites and desorption with ethanol but these products have distinctly different hydrophobicities and structures and thus such a method is not obviously applicable here.

Improvement in processes for purifying 1,3-propanediol, glycerol, or a mixture of 1,3-propanediol and glycerol from fermentation broth, particularly with respect to product recovery, energy consumption, and feedback inhibition, are needed. A technique which would selectively remove the 1,3-propanediol during the fermentation reaction would be of tremendous utility. Such a technique would be expected to decrease the available 1,3-propanediol concentration, thereby removing feedback inhibition and increasing the total production rate of 1,3-propanediol. As a result, higher capital productivity and potentially higher reaction yields would be achieved.

SUMMARY OF THE INVENTION

Applicants provide a process for separating material from a mixture comprising the steps of: (a) contacting a biological mixture containing 1,3-propanediol, glycerol, or 1,3-propanediol and glycerol with a sufficient amount of a zeolite selected from the group consisting of MFI, MEL, BEA, MOR, FAU, LTL, GME, FER, MAZ, OFF, AFI, AEL, and AET and materials of the same topology as these zeolites; (b) contacting the zeolite of step (a) with a desorbant such as an ethanol:water solution or any $C_1$–$C_4$ alcohol:water solution; (c) collecting the 1,3-propanediol, glycerol, or mixture of 1,3-propanediol and glycerol eluted from the zeolite in step (b); and (d) optionally repeating the series of steps (a) through (c) at least one time. Additionally, the process includes selecting in step (a) a first zeolite to selectively adsorb a mixture of 1,3-propanediol and glycerol from the biological mixture, and after performing the series of steps (b), (c), and optionally (d), then performing step (a)' by contacting the mixture of 1,3-propanediol and glycerol with a second zeolite to selectively adsorb 1,3-propanediol or glycerol from the mixture of 1,3-propanediol and glycerol, (b)' contacting the zeolite of step (a)' with a desorbant such as an ethanol:water solution or any $C_1$–$C_4$ alcohol:water solution; (c)' collecting the 1,3-propanediol or glycerol eluted from the molecular sieve in step (b)'; and (d)' optionally repeating the series of steps (a)' through (c)' at least one time to obtain a purified 1,3-propanediol or glycerol.

DETAILED DESCRIPTION OF THE INVENTION

Figure 1:
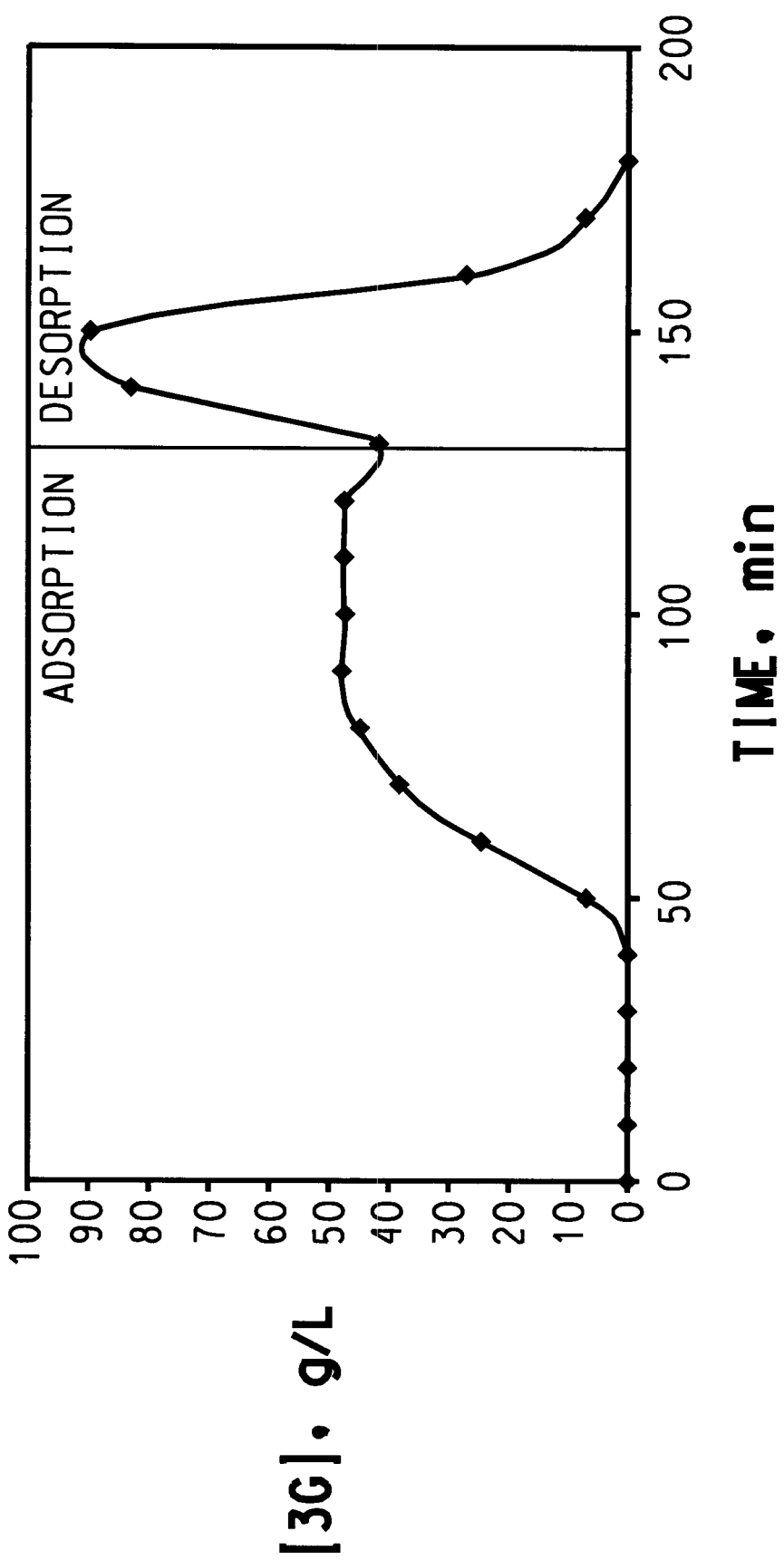
FIG. 1 shows the zeolite packed column adsorption of 1,3-propanediol from cell-free fermentation broth and desorption of 1,3-propanediol using ethanol:water.

The present invention provides a new technique for the separation of 1,3-propanediol, glycerol, or a mixture of 1,3-propanediol and glycerol from biological mixtures using a molecular sieve. The method of the present invention makes use of relatively simple equipment and easy maintenance when compared to other available methods. Also, the method resolves the major problem of the high cost of currently available adsorbents and the product variability.

Selectively concentrated product is provided in accordance with this invention by contacting a cell-free broth with a zeolite-sorbent selected from a group of molecular sieves at a temperature and flow rate suitable for sorption, for a period of time sufficient to remove impurities associated with the broth and enrich 1,3-propanediol.

Where enriched 1,3-propanediol product is desired, the invention also includes a process for desorbing sorbed 1,3-propanediol to provide a product which is enriched therewith. The process, based upon adsorption/desorption, is particularly useful for high product recovery where the product is recovered in ethanol instead of water and therefore is less costly to distill.

In the purification process, additional impurities may be present in the product. It is preferred that a principal compound (e.g., 1,3-propanediol, glycerol, or both 1,3-propanediol and glycerol together), be entirely removed selectively, not only from the fermentation, but also from other contaminants, by-products, or substrates such as glucose, glycerol, etc. One skilled in the art understands that such selective removal is uncommon. In most instances, a sorbent has the ability to remove more than the target compound and thus the cost of removing the target compound increases and a secondary purification problem arises when the sorbent is regenerated. By selecting the proper molecular sieve(s) and utilizing a programmed solvent desorption of sorbed 1,3-propanediol, a separation of 1,3-propanediol, glycerol, or of 1,3-propanediol and glycerol together from other broth components can be achieved.

In the application, unless specifically stated otherwise, the following abbreviations and definitions apply:

"In situ product removal" is abbreviated ISPR.

"Volumetric productivity" refers to the mass of product produced in a given volume per time, with units of grams/(liter hour), abbreviated g/(L hr).

"Titer" refers to the product concentration in the liquid phase, with units of grams/liter, abbreviated g/L.

"1,3-propanediol" is abbreviated 3G.

"Qmax" and "Km" refer to the Langmuir parameters of maximum adsorbent loading and adsorbate concentration at Qmax/2, respectively. Typical units are grams adsorbate/gram adsorbent (g/g), and grams/liter (g/L), respectively.

Molecular sieves are well known in the art and are defined in R. Szosak, Molecular Sieves-Principles of Synthesis and Identification, Van Nostrand Reinhold (1989) at page 2. Additional useful general references relating to zeolite structure and characterization include the following: Meier et al. Atlas of Zeolite Structure Types (International Zeolite Assn. 1978); Mumpton, "Natural Zeolites" in Reviews in Mineralogy 14:1 (1977); Smith, "Origin and Structure of Zeolites" in Zeolite Chemistry and Catalysis, ACS Monograph 171 (American Chemical Society, (1976); Breck, "Zeolite Molecular Sieves" (Wiley, 1974); Dyer, "An Introduction to Zeolite Molecular Sieves" (John Wiley & Sons, 1988); Szostak, "Handbook of Molecular Sieves" (Van Nostrand Reinhold, 1992).

A class of zeolite species employed in the process of the present invention, is a medium-pore synthetic zeolite that in the as-synthesized form can be described by the formula: $(Na,TPA)_n[Al_nSi_{96-n}O_{192}]$~16 $H_2O$ for ZSM-5 and $(Na, TBA)_n[Al_nSi_{96-n}O_{192}]$~16 $H_2O$ for ZSM-11, where TPA, and TBA are tetrapropylammonium and tetrabutylammonium cations, respectively. The structure and synthesis of these synthetic zeolites are well known in the relevant art. These zeolites can then be converted to a hydrogen form by standard procedures well known in the art (Donald W. Breck; Zeolite Molecular Sieves; supra. When the balancing cation in the zeolite is $H^+$, then the framework is a solid acid that can reveal shape-selective catalytic or adsorptive properties due to confinement of the acidic proton within the zeolite pore architecture. The H-ZSM-5 has an average pore size of 5.5 Angstroms.

In one embodiment, the present invention employs H-ZSM-5 for 1,3-propanediol separation from a cell free broth. Furthermore, ethanol/water is used for desorption of 1,3-propanediol from ZSM-5 zeolite. Unexpectedly, the adsorbed 1,3-propanediol was displaced by the ethanol/water mixture. Moreover, the yield of 1,3-propanediol was increased by increasing the concentration of ethanol, which indicates the desirability of performing the elution of 1,3-propanediol by an ethanol-rich mixture. Total recovery of 1,3-propanediol product was calculated to be as high as 94.7%. Although the instant invention utilizes ethanol to elute the adsorbed 1,3-propanediol, any $C_1$–$C_4$ alcohol is within the scope of the present of the present invention. 1,3-Propanediol desorption is performed at room temperature. However, it is expected that temperatures between room temperature and 80° C. will produce the described useful effect.

In an alternate embodiment, a two-step programmed desorption is achieved by feeding the column with an increasing concentration of ethanol. The first low concentration resulted in eluting the nondesired compounds while the second higher concentration eluted predominantly 1,3-propanediol. This process reduced the level of contamination of 1,3-propanediol with other components.

Figure 3:
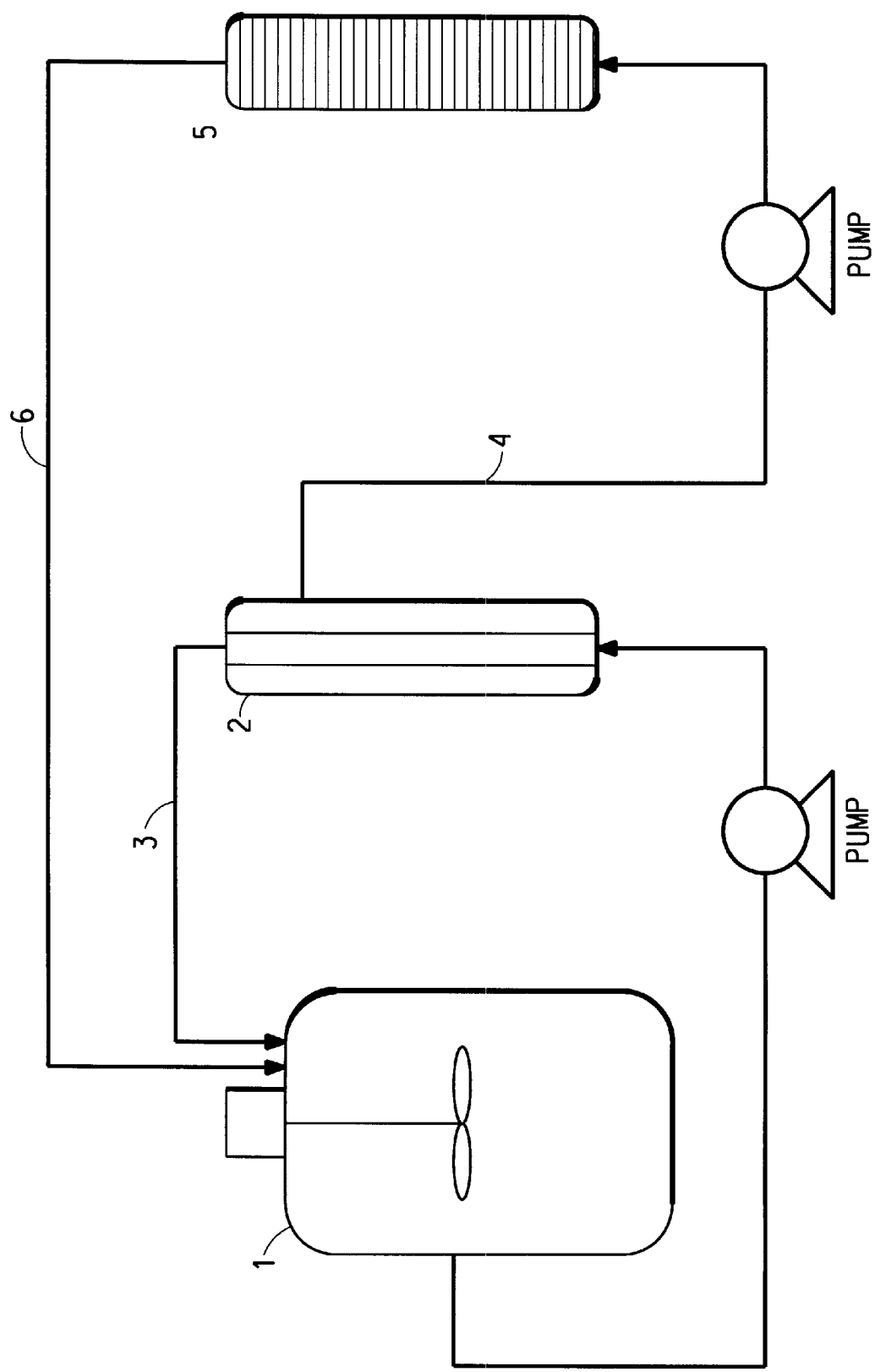
FIG. 3 shows a schematic of the ISPR Equipment Setup. A fermenter (1) is connected to crossflow filtration membranes (2) for cell mass removal. The retentate (3) is recycled to the fermenter (1). Permeate (4) is sent through the zeolite-packed column (5) and the spent fluid (6) returned to the fermenter (1). Dual cell filters and zeolite columns are used for redundancy.

In a preferred embodiment, a fermentation vessel (1) is set up with a broth recirculation loop, which included a cross-flow filtration unit (2) and a column (5) filled with H-ZSM-5, for in situ removal of 1,3-propanediol from the fermentation. An inocculum of E. coli capable of producing 1,3-propanediol from glucose was added to the fermenter (1). The setup allowed removal of broth from the fermenter (1) permitting the return of the biocatalyst cells to the fermenter while the cell-free broth was passed through the zeolite column (5) to remove 1,3-propanediol. The broth was ultimately returned to the fermenter (FIG. 3). The procedure is performed with two ISPR periods which increased the production rate to the highest rate of the entire run. This result demonstrates the positive effect of the ISPR. For use with a fermentation broth, cross-flow filtration is used to remove the cells before to contacting the broth with the molecular sieve. Other solid-liquid separation methods such as centrifugation, dead-end filtration, or tangential flow filtration can also be used.

In an alternate embodiment, the zeolite H-ZSM-5 (Si/Al=140) is used for batch 1,3-propanediol removal from the cell-free fermentation. The demonstrated numbers for 1,3-propanediol adsorption (0.132 g/g) exceed those obtained in the art (e.g., Schollner et al.) by 33% or more; the theoretical loadings (0.17 g/g Qmax from Langmuir fit) exceed those in the art by 80% or more. The substantially greater loading means that less zeolite material is needed and hence a smaller adsorber and capital expense would be required for the same process. Alternatively, the same quantity of zeolite can be used with fewer required desorption cycles and less solvent usage which would further decrease the operating expense.

In another embodiment, a number of molecular sieves are examined for their 1,3-propanediol, glycerol, or 1,3-propanediol and glycerol loading capacity. Surprisingly, molecular sieves such as H-ZSM-5 zeolite (Si/Al=140) and H-ZSM-5 zeolite (Si/Al=150) had the two highest total loadings and the relative selectivity of 1,3-propanediol and glycerol were found to be dependent on the choice of the molecular sieve.

In another embodiment, 1,3-propanediol and glycerol are simultaneously removed from the fermentation broth by using zeolite H-ZSM-5 zeolite (Si/Al=500) or H-ZSM-5 zeolite (Si/Al=15), either of which has high total loadings and has 1,3-propanediol:glycerol selectivity close to unity. The resulting 1,3-propanediol/glycerol mixture is then separated using a gradient elution as described below. The mixture can also be further purified using conventional separation methods such as distillation.

In yet another embodiment, 1,3-propanediol is removed from the fermentation broth using a molecular sieve with high selectivity for 1,3-propanediol/glycerol as described above, and the fermentation broth is then treated with a molecular sieve with high loading for glycerol (e.g., H-ZSM-5 zeolite, Si/Al=15) to remove the valuable glycerol component. Combinations of the above methods, to recover 1,3-propanediol, glycerol, or a mixture 1,3-propanediol and glycerol either sequentially or in parallel, are within the scope of the present invention.

Moreover, it is discovered that using any of the above mentioned molecular sieves in a separation step and ethanol in an elution step achieves a yield greater than 90%. H-ZSM-5 (a particular form of MFI) is chosen for this means of purification; however it will be appreciated by the skilled artisan that a variety of zeolites will be suitable. Other zeolites for the purpose of the present invention can be selected from a group consisting of MFI, MEL, BEA, MOR, FAU, LTL, GME, FER, MAZ, OFF, AFI, AEL, and AET and materials of the same topology as these specific zeolites. Preferred structures include FAU, MFI, MEL, and BEA. These molecular sieves are well known in the art and are described by W. M. Meier et al. (Atlas of Zeolite Structure Types, $4^{th}$ edition, supra). Examples of these molecular sieves might include but are not limited to those with high Si/Al ratios (e.g., $\geq 5$) indicating the acidity, hydrophobocity, pore size, and other characteristics of a particular zeolite framework. Selectivities can be further improved by physical treatments such as drying and/or chemical treatments such as modifying the molecular sieve with a coating. Specifically, a coating of a molecular sieve, which include zeolites, can be accomplished in the following manner: (1) a sample of the molecular sieve is exposed to the ambient atmosphere and is immersed in tetraethylorthosilicate (TEOS) for 2 hours; (2) the sample is filtered and dried at room temperature overnight; (3) the sample is then heated in flowing nitrogen at 550° C. for 3 hours. The preceding treatment can be performed with one or more compounds containing at least one element selected from silicon, aluminum, boron and phosphorus, to deposit substantially on the external surfaces of the molecular sieve at least 0.05 weight % of the element. The coating can also be performed on non-listed molecular sieves which can yield sorbent for the purpose of the invention. Molecular sieve forms can include but not limited to those in powder, extrudate, granules, part or whole of a membrane, or the like.

It is further discovered that silica binders are more stable to long term aqueous exposure for use in the invention.

Separation of 1,3-propanediol, glycerol, or a mixture of 1,3-propanediol and glycerol utilizing the above-described molecular sieves make use of relatively simple equipment and provide easy maintenance when compared to the known separation procedures. As will be seen below, zeolites having a pore size much smaller from those described above have very different adsorptive properties and will not be capable of selectively adsorbing 1,3-propanediol.

In summary, this invention selectively separates 1,3-propanediol, glycerol, or a mixture of 1,3-propanediol and glycerol from a mixture of contaminants, by-products and co-product compounds using specific molecular sieves. It further concentrates them during the separation using specific desorbents. It still further minimizes the cost of the following distillation or purification.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C. (1994) or in *Biotechnology: A Textbook of Industrial Microbiology*; Brock, T. D., $2^{nd}$ ed.; Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "h" means hour(s), "d" means day(s), "μL" means microliter(s), "mL" means milliliter(s), "L" means liter(s), "mM" means millimolar, "M" means molar, "mmol" means millimole(s), "g" means gram(s), "μg" means microgram(s) and "ng" means nanogram(s), "v:v" means volume per volume.

Identification and Measuring the Concentration of 3G and Glycerol 1,3-Propanediol and glycerol may be identified directly by submitting the media to high pressure liquid chromatography (HPLC) analysis. Preferred in the present invention is a method where fermentation media is analyzed on an analytical ion exchange column using a mobile phase of 0.01 N sulfuric acid in an isocratic fashion. In all of the examples the concentration of 3G was measured by HPLC or GC.

A Waters 717 autosampler, Waters temperature control module (T=50° C.), Waters 410 differential refractometer, and Waters 486 absorption detector (I=210 nm) was equipped with a Shodex HPLC column (SH1011 sugar column, 300 mm×8 mm) for 1,3-propanediol quantitation. Mobile phase was 0.005M $H_2SO_4$ at 0.5 ml/min isocratic flow. Pivalic acid was used as an internal standard. Under these conditions, 1,3-propanediol and glycerol elute at 26.7 min and 21.2 min, respectively.

Production of 1,3-propanediol was confirmed by GC/MS. Analyses were performed using standard techniques and materials available to one of skill in the art of GC/MS. One suitable method utilized a Hewlett Packard (HP) 6890 GC equipped with an HP Innowax polyethylene glycol column (HP19091N-133, 30 m×250 mm×0.25 mm) was used for 1,3-propanediol quantitation. Detection was done with a flame ionization detector. The oven profile was 100° C. at t=0, ramped to 250° C. by t=3 minutes, held at 250° C. until t=5 minutes. Helium flow was 2 ml/min. Sample injection volume was 1 ml. Under these conditions, 1,3-propanediol and glycerol elute at 2.5 min and 3.65 min, respectively.

Media and Carbon Substrates

*E. coli* strain FM5 pAH48/pDT29 was used in all fermentations described below.

Fermentation media in the present invention must contain suitable carbon substrates. Suitable substrates may include but are not limited to monosaccharides (such as glucose and fructose), oligosaccharides (such as lactose or sucrose), polysaccharides (such as starch or cellulose or mixtures thereof) and unpurified mixtures from renewable feedstocks (such as cheese whey permeate, cornsteep liquor, sugar beet molasses, and barley malt). Additionally, the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has been reported in methylotrophic yeasts (Yamada et al. *Agric. Biol. Chem.* 53(2), 541–543 (1989)) and in bacteria (Hunter et.al., *Biochemistry* 24, 4148–4155 (1985)). These organisms can assimilate single carbon compounds, ranging in oxidation state from methane to formate, and aproduce glycerol. The pathway of carbon assimilation can be through ribulose monophosphate, through serine, or through xylulose-momophosphate (Gottschalk, *Bacterial Metabolism*, Second Edition, Springer-Verlag: New York (1986)). The ribulose monophosphate pathway involves the condensation of formate with ribulose-5-phosphate to form a 6-carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al. *Microb. Growth Cl Compd.* [Int. Symp.], $7^{th}$, 415–32 (1993). Editor(s): Murrell, J. Collin; Kelly, Don P. Publisher: Intercept, Andover, UK). Similarly, various species of Candida will metabolize alanine or oleic acid (Sulter et al. *Arch. Microbiol.* 153(5), 485–9 (1990)). Hence, it is contemplated that the source of carbon utilized in the present invention may encompass a wide variety of carbon-containing substrates and will only be limited by the choice of organism.

Although it is contemplated that all of the above mentioned carbon substrates and mixtures thereof are suitable in the present invention, preferred carbon substrates are glucose, fructose, sucrose, or methanol.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Culture Conditions

Typically, cells are grown at 30° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly (e.g., cyclic adenosine 2':3'-monophosphate), may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations.

Suitable pH ranges for the fermentation are between pH 5.0 to pH 9.0 where pH 6.0 to pH 8.0 is preferred as the initial condition.

Reactions may be performed under aerobic or anaerobic conditions where anaerobic or microaerobic conditions are preferred.

Batch and Continuous Fermentations

The present process employs a batch method of fermentation. Classical batch fermentation is a closed system where the composition of the media is set at the beginning of the fermentation and not subjected to artificial alterations during the fermentation. Thus, at the beginning of the fermentation the media is inoculated with the desired organism or organisms and fermentation is permitted to occur without further addition to the system. Typically, however, "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentation are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Cells

Cells suitable in the present invention comprise those that harbor a dehydratase enzyme. Typically the enzyme will be either a glycerol dehydratase or a diol dehydratase having a substrate specificity for either glycerol or 1,2-propanediol, respectively. Dehydratase enzymes are capable of converting glycerol to hydroxypropionaldehyde (3-HPA) which is then converted to 1,3-propanediol. Cells containing this pathway may include mutated or recombinant organisms belonging to the genera Citrobacter, Enterobacter, Clostridium, Klebsiella, Samonella, and Lactobacillus. Microorganisms known by persons skilled in the art to produce glycerol by fermentation, e.g., Aspergillus, Saccharomyces, Zygosaccharomyces, Pichia, Kluyveromyces, Candida, Hansenula, Dunaliella, Debaryomyces, Mucor, Torylopsis, and Methylobacteria, may be the hosts for a recombinant dehydratase enzyme. Other cells suitable as hosts in the present invention include Bacillus, Escherichia, Pseudomonas and Streptomyces. It is believed that organisms, belonging to the above mentioned groups, exist in nature that are suitable for the present invention.

Zeolites used as the molecular sieves may be obtained from various manufacturers including Zeolyst (formerly PQ) (Valley Forge, Pa.), Süd-Chemie (Germany), UOP (Des Plaines, Ill.), Uetikon (Switzerland).

Example 1

Selective Concentration of 1,3-Propanediol via Column Adsorption/Desorption 23 g extrudate (⅛ inch diameter) of H-ZSM-5 (~75% H$^+$, 25% Na$^+$cation balance; Si:Al=25; 70% zeolite, 30% alumina binder) was packed into an Amicon column (Millipore Corporation, Bedford, Mass.) (40 ml column volume, ~1" ID) and cell-free broth (47 g/L 1,3-propanediol) was pumped through the column at 0.8 ml/min. This flow continued until 1,3-propanediol breakthrough of the column was observed (i.e., when the exit concentration of 1,3-propanediol equaled the inlet concentration (t=90 min)). At t=120 min, 50:50 (v:v) ethanol: H$_2$O was pumped through the column at 0.8 ml/min to elute the adsorbed 1,3-propanediol product (FIG. 1).

Mass of adsorbed 1,3-propanediol was 2.10 g and mass of desorbed 1,3-propanediol was 1.99 g; calculated recovery of product was 94.7%.

Example 2

Programmed Solvent Desorption of Adsorbed 1,3-Propanediol

A column (1 L volume; 1.875" ID) packed with H-ZSM-5 zeolite (see Example 1) was previously contacted with a cell-free broth mixture of 1,3-propanediol, glycerol, glucose, and other components (feed concentration: 8.0 g/L 1,3-propanediol, 29.7 g/L glycerol). Two-step programmed desorption was achieved by feeding the column (10 ml/min) with 5% EtOH/95% H$_2$O followed by 50% EtOH/50% H$_2$O. The 5% EtOH/95% H$_2$O eluted the nondesired glycerol, while the 50% EtOH/50% H$_2$O eluted predominantly 1,3-propanediol. The 5% EtOH/95% H$_2$O step (t<23 minutes) gave a fraction consisting of 5.8 g glycerol and 1.8 g 1,3-propanediol (mass ratio glycerol:1,3-propanediol=3.17). The 50% EtOH/50% H$_2$O step (t>23 minutes) gave a fraction consisting of 9.29 g glycerol and 13.5 g 1,3-propanediol (mass ratio 1,3-propanediol:glycerol=1.46). The 50% EtOHW50% H$_2$O step therefore has significantly increased the proportion of 1,3-propanediol:glycerol relative to the feed (mass ratio 1,3-propanediol:glycerol=0.27).

Figure 2:
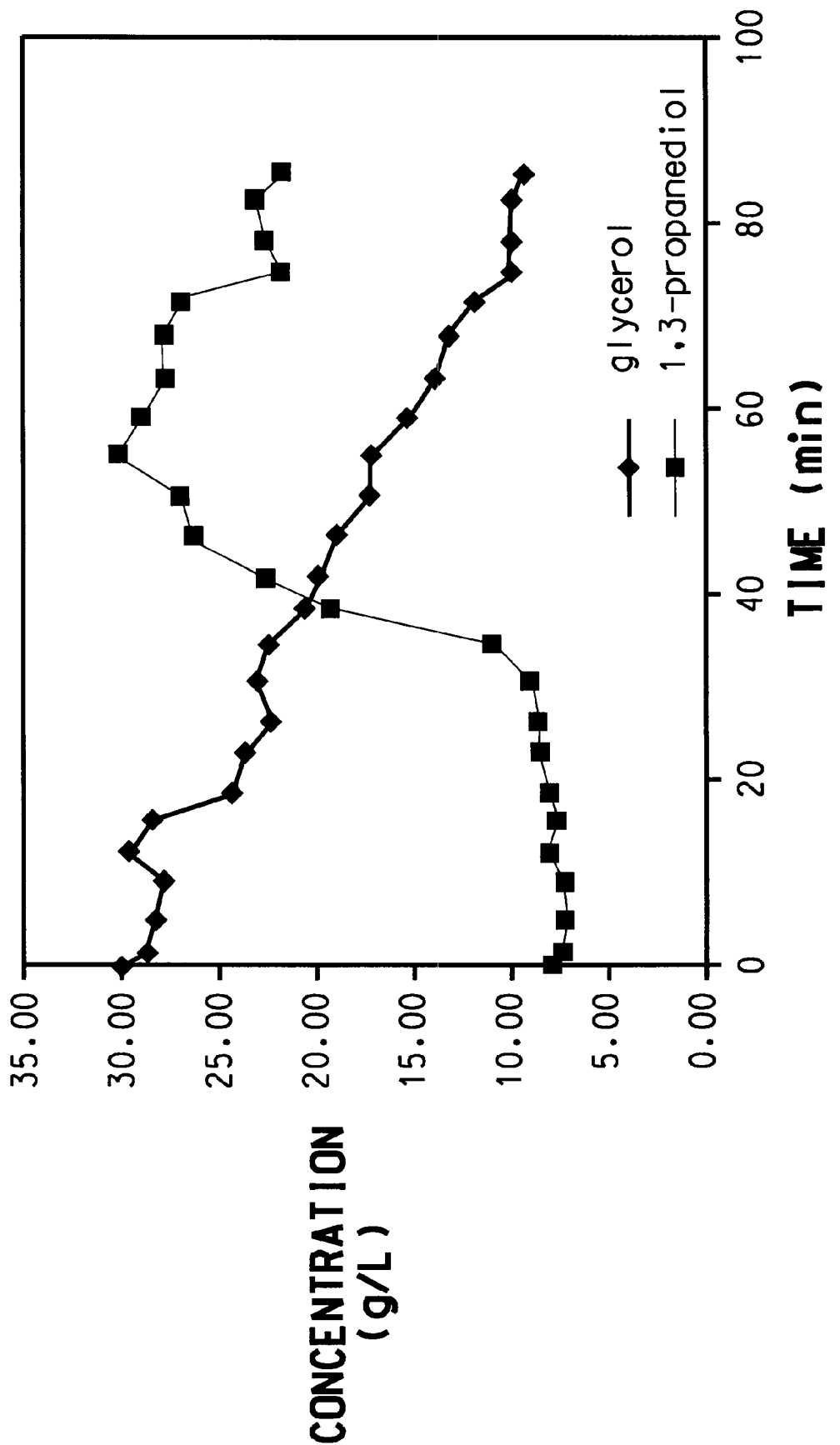
FIG. 2 shows the elution of 1,3-propanediol from a larger-scale zeolite column.

Further, this 50% EtOH:50% H$_2$O eluent with 1,3-propanediol required less heat input due to the lower latent heat of ethanol relative to water. The programmed elution, here done in two steps, therefore resulted in a glycerol-rich fraction and a 1,3-propanediol-rich fraction, which otherwise may have eluted together (FIG. 2).

Example 3

In-situ 1,3-Propanediol Removal from Fermentation Broth

Figure 4:
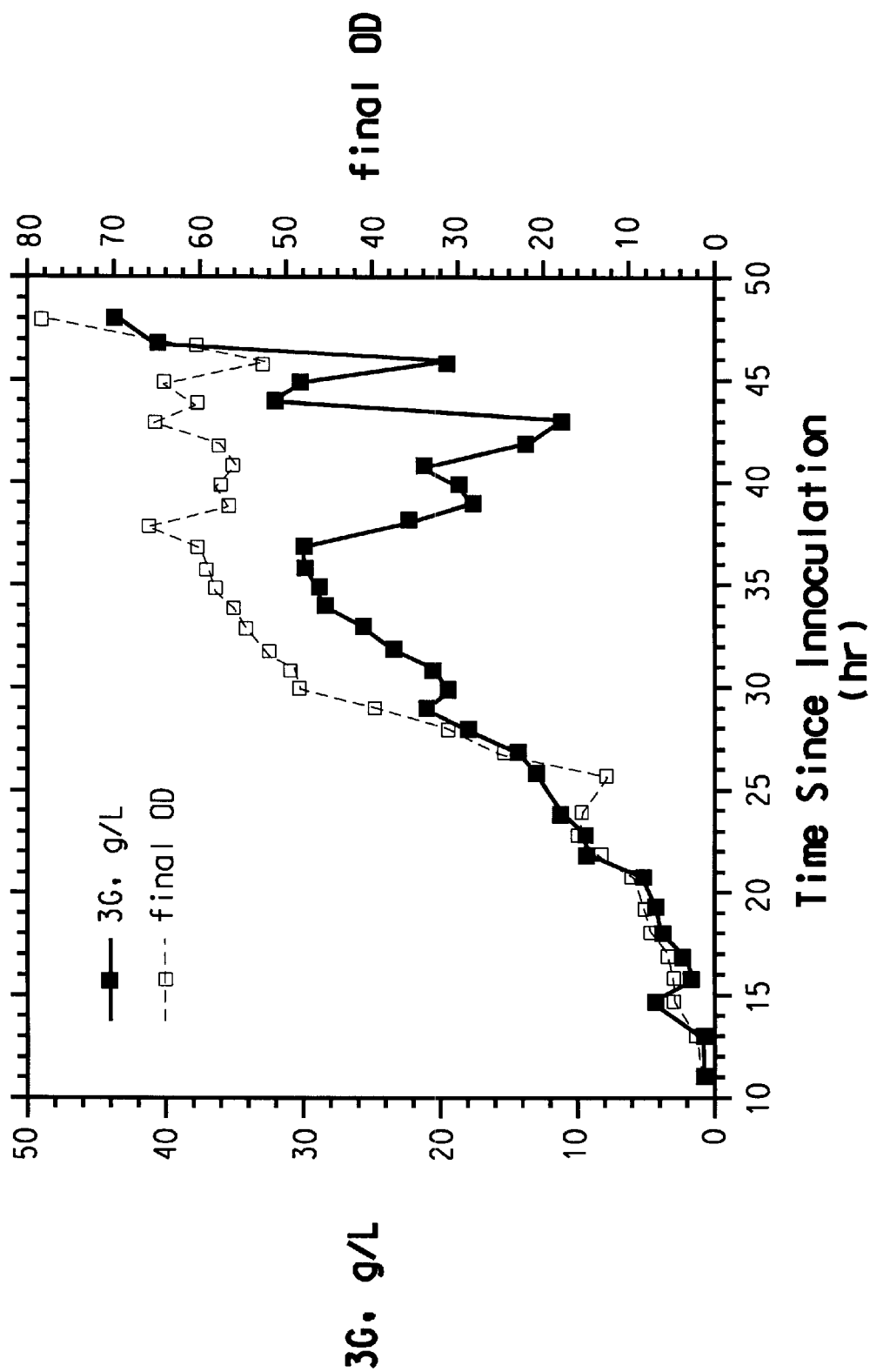
FIG. 4 shows the titer of a 2L 1,3-propanediol fermentation before, during, and after two periods of ISPR.

A 2 L fermentation vessel (1) (1.5 L active volume) was set up with a broth recirculation loop which included a cross-flow filtration unit (2) and a column (5) (1 L volume; 1.875 "ID) filled with H-ZSM-5 zeolite extrudate (identical in composition to that used in Example 1), as illustrated in FIG. 3. An inocculum of E. coli (FM5 pAH48pDT29) capable of producing 1,3-propanediol from glucose was added to the fermenter. Using the set up described above, the fermenter (1) was run for 35 h without ISPR. At 35 h, the fermentation showed a slow down in 1,3-propanediol production (0.8 g/L hr) and cell mass, indicative of impending fermentation failure. After the first ISPR period (60 min duration; flow to filter 6 ml/min), the rate of 1,3-propanediol production increased almost threefold to 2.1 g/L hr. After the second ISPR period (112 min duration; flow to filter 6 ml/min), the production rate further increased to more than 5 g/L hr. Total concentration of 1,3-propanediol produced, including the amount adsorbed, exceeded 60 g/L. This number represents a 100% increase over the base case (30 g/L at 36 h). Total volumetric productivity (g/L h) increased by 40% compared to the base case. Further production of 1,3-propanediol post-37 h occurred with little cell growth, as measured by final OD (FIG. 4).

Example 4

Batch 1,3-Propanediol Removal from Cell-Free Fermentation Broth

H-ZSM-5 (Si/Al=140; wt % Na$_2$O=0.02; crystallite of 0.5 μm) was tested for adsorption of 1,3-propanediol from cell-free fermentation broth. Zeolite was batch contacted for 24 h with agitation (200 rpm) at room temperature (nominal 22° C.). Liquid samples were then withdrawn for quantitation of 1,3-propanediol and glycerol.

| [3G]-initial, g/L | [3G]equil, g/L | [gly]initial, g/L | [gly]equil, g/L | 3G loading, g/g | glycerol loading, g/g | selectivity (3G/gly) |
|---|---|---|---|---|---|---|
| 83.16 | 68.15 | 6.86 | 6.69 | 0.132 | 0.002 | 83.860 |
| 41.58 | 30.14 | 3.43 | 1.00 | 0.115 | 0.025 | 4.705 |
| 20.79 | 13.39 | 1.72 | 0.00 | 0.073 | 0.017 | 4.311 |
| 8.316 | 5.53 | 0.69 | 0.00 | 0.026 | 0.007 | 4.053 |

Demonstrated loadings of greater than 0.13 g 1,3-propanediol/g zeolite were achieved. With a Langmuirian fit to the data, maximum theoretical loadings were calculated to be 0.178 g/g ($r^2$=0.996) with Km of 20.4 g/L 3G.

Example 5

Batch 1,3-Propanediol and Glycerol Adsorption from Fermentation Broth

Equilibrium adsorption loadings were determined in batch by contacting cell-free fermentation broth with a molecular sieve or zeolite. Adsorbent was batch contacted for 24 h with agitation (200 rpm) at room temperature (nominal 22° C.). Liquid samples were then withdrawn for quantitation of 1,3-propanediol and glycerol.

Figure 5:
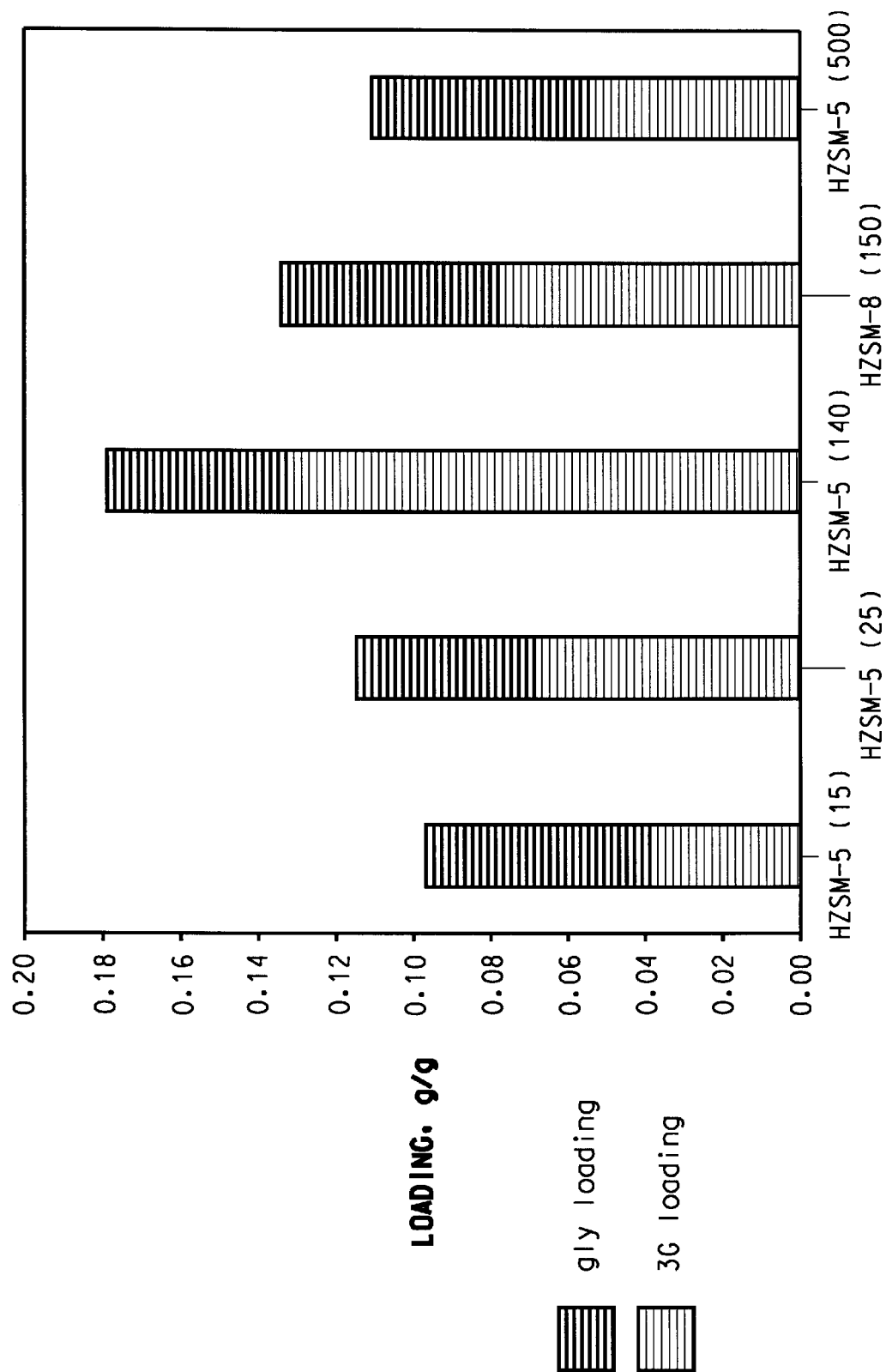
FIGS. 5 and 6 show the batch adsorption loading of 1,3-propanediol and glycerol, respectively, from cell-free fermentation broth. The x-axis indicates the type of zeolite with the Si/Al ratio shown in parentheses. The scales used on FIGS. 5 and 6 are identical.

As shown in FIG. 5, H-ZSM-5 (Si/Al=140) (further defined in Example 4) not only gave the best performance of the zeolites examined, in terms of total loading of 1,3-propanediol and glycerol (0.179 g/g total loading) but also in terms of selectivity for 1,3-propanediol (2.82:1 1,3-propanediol:glycerol).

Figure 6:
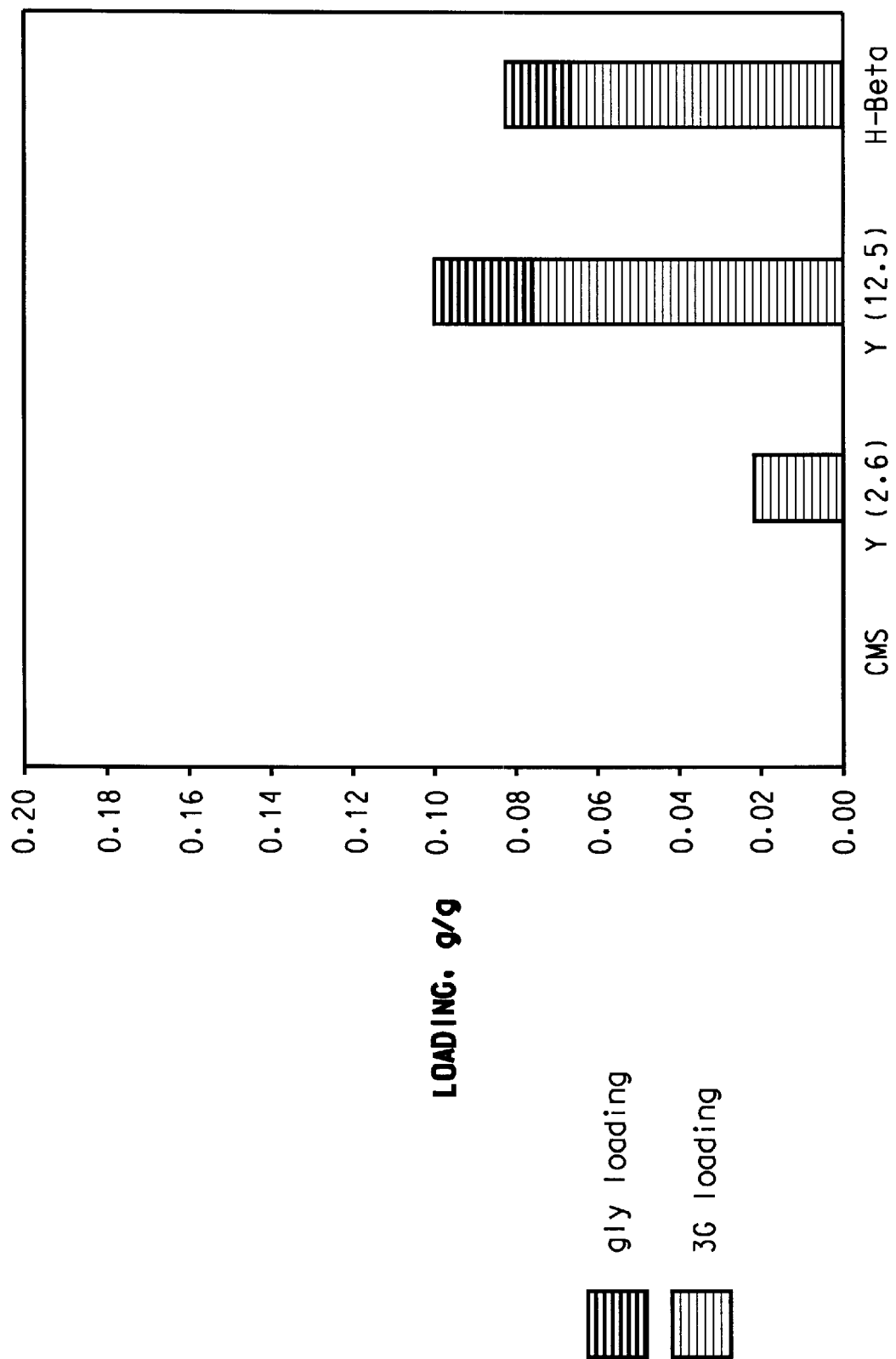

As shown in FIG. 6, CMS molecular sieve (commercially available molecular sieve) and H-Beta zeolite were also examined. CMS, a small pore carbon molecular sieve, gave no detectable loading; H-Beta, a large pore zeolite, gave moderate loading (0.083 g/g total loading) and good selectivity (3.88:1 1,3-propanediol:glycerol).

Example 6

Longer Term Zeolite Operation in Aqueous Environment

The zeolite was used with a binder for mechanical strength in packed bed operation. The mass of the zeolite-binder was measured over 24 h in batch with agitation (200 rpm) before vacuum filtration with a cellulose acetate filter. Final zeolite mass was measured by the dry weight of zeolite remaining on the filter. The results indicate that the alumina binder becomes solubilized much more readily (1300%) than the silica case and indicate that a silica binder is preferable for long term operation in aqueous environments.

| zeolite | extrudate binder | initial zeo, g | final zeo, g | % zeo mass loss |
|---|---|---|---|---|
| H-ZSM-5 (I) | Alumina | 2.641 | 2.2981 | 12.98 |
| H-ZSM-5 (II) | Silica | 2.667 | 2.6406 | 0.99 |
| NaZSM-5 (III) | Alumina | 2.67 | 2.3264 | 12.87 |

The zeolite descriptions are as follows: H-ZSM-5 (I) (Si/Al=14.8 after addition of Al binder; %Na=0.08%), H-ZSM-5 (II) (silica binder); Na-ZSM-5 (III) (Si/Al=15) formed by contacting three times with 2 L of an aqueous 10% $NaNO_3$ solution at 90° C. for 1 hour each time. The resulting material was calcined in air by raising the temperature 60° C. per h to 500° C., holding at 500° C. for 10 min, then raising the temperature once again at a rate of 60° C. per h to 550° C., holding at 550° C. for 5 h, cooling to 110° C. and placing the resulting material in a dry vial and sealing.

What is claimed is:

1. A method for separating 1,3-propanediol, glycerol or a mixture of 1,3-propanediol and glycerol selectively from a mixture comprising the steps of:

(a) contacting a mixture containing a mixture of 1,3-propanediol and glycerol with a sufficient amount of a first zeolite selected from the group consisting of MFI, MEL, BEA, MOR, FAU, LTL, GME, FER, MAZ, OFF, AFI, AEL, and AET, and materials with the same topology as these zeolites, the zeolite selected on the basis of its selectivity to 1,3-propanediol and glycerol approaching unity;

(b) contacting tie first zeolite of step (a) with a desorbant of an ethanol:water solution or any $C_1$–$C_4$ alcohol:water solution;

(c) collecting the 1,3-propanediol and glycerol eluted from the zeolite in step (b);

(d) repeating steps (a) through (c) at least one time with the 1,3-propanediol and glycerol collected in step (c); and (e) performing step (a)' by contacting the mixture of 1,3-propanediol and glycerol of steps (c) or (d) with a second zeolite to selectively adsorb 1,3-propanediol or glycerol, (b)' contacting the second zeolite of step (a)' with a desorbant of an ethanol:water solution or of any $C_1$–$C_4$ alcohol:water solution, (c)' collecting the 1,3-propanediol or glycerol eluted from the zeolite in step (b)', and (d)' repeating the series of steps (a)' through (c)' at least one time to obtain a purified 1,3-propanediol or glycerol.

2. The process of claim 1 wherein the first and the second zeolite are each bound in a molecular sieve comprising a binder selected from the group consisting of alumina and silica.

3. The process of claim 2 wherein either the first or the second zeolite is MFI(H-ZSM-5).

4. The process of claim 3 wherein the desorbant is an ethanol:water solution.

* * * * *